US009109195B2

(12) United States Patent
Zimmermann et al.

(10) Patent No.: US 9,109,195 B2
(45) Date of Patent: Aug. 18, 2015

(54) APPARATUS AND METHOD FOR THE DEPOSITION OF BIOLOGICAL MATERIAL IN A TARGET SUBSTRATE

(75) Inventors: Heiko Zimmermann, St. Ingbert (DE); Guenter R. Fuhr, Berlin (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 405 days.

(21) Appl. No.: 12/514,338

(22) PCT Filed: Jan. 28, 2008

(86) PCT No.: PCT/EP2008/000642
§ 371 (c)(1),
(2), (4) Date: May 11, 2009

(87) PCT Pub. No.: WO2008/092619
PCT Pub. Date: Aug. 7, 2008

(65) Prior Publication Data
US 2010/0062529 A1 Mar. 11, 2010

(30) Foreign Application Priority Data

Jan. 31, 2007 (DE) ........................ 10 2007 004 855

(51) Int. Cl.
*C12M 1/00* (2006.01)
*C12N 5/00* (2006.01)
(Continued)

(52) U.S. Cl.
CPC ............... *C12M 35/08* (2013.01); *C12M 35/00* (2013.01); *C12M 41/12* (2013.01)

(58) Field of Classification Search
CPC ...... C12M 35/00; C12M 41/12; C12M 35/08; A61B 18/20; B41M 5/38207; B41M 5/385; B41M 5/41; B41M 5/465; C12N 13/00; C12N 15/87; C12N 15/8207; C23C 14/048; C23C 14/28; G01N 1/281; G01N 2001/2886; B01J 2219/00641; B01J 2219/00659; B01J 2219/00725; B01J 2219/00743; B01J 2219/00527; B01J 2219/00603; A61K 47/48861
USPC .................................... 435/285.3, 307.1, 379
See application file for complete search history.

(56) References Cited

U.S. PATENT DOCUMENTS 5,036,006 A 7/1991 Sanford et al.
5,219,746 A * 6/1993 Brinegar et al. .................. 435/6
(Continued)

FOREIGN PATENT DOCUMENTS

DE 69732106 T2 12/2005
EP 0331855 A2 9/1989
(Continued)

*Primary Examiner* — William H Beisner
*Assistant Examiner* — Danielle Henkel
(74) *Attorney, Agent, or Firm* — Caesar Rivise, PC

(57) ABSTRACT

Disclosed is a deposition apparatus (100) which is designed to deposit frozen biological material (1) in a target substrate (2) and includes a charging device (10) and a driving device (20). The charging device (10) is designed to supply the biological material (1) to the driving device (20) while the driving device (20) is designed to apply a driving force to the biological material (1). In order to apply the driving force, the driving device (20) is formed such that the biological material (1) can penetrate into the target substrate (2) under the effect of the driving force. Also disclosed are an injector cartridge which is designed to provide frozen biological material in a deposition apparatus as well as a method for depositing biological material (1) in a target substrate (2).

34 Claims, 8 Drawing Sheets

(51) Int. Cl.
*C12M 1/42* (2006.01)
*C12M 1/34* (2006.01)

(56) References Cited

U.S. PATENT DOCUMENTS

| | | | |
|---|---|---|---|
| 6,053,889 A * | 4/2000 | Heinzen et al. | 604/68 |
| 2005/0018036 A1* | 1/2005 | Barron et al. | 347/224 |
| 2005/0214946 A1 | 9/2005 | Bebee | |
| 2005/0226885 A1 | 10/2005 | Soegaard et al. | |
| 2006/0134600 A1 | 6/2006 | Fuhr et al. | |
| 2006/0246042 A1* | 11/2006 | Davies | 424/93.7 |

FOREIGN PATENT DOCUMENTS

| | | | | |
|---|---|---|---|---|
| EP | 1637173 A2 | 3/2006 | | |
| EP | 1649885 A1 | 4/2006 | | |
| WO | 9407603 A1 | 4/1994 | | |
| WO | WO98/10750 | * | 3/1998 | A61K 9/16 |
| WO | 2004074426 A2 | 9/2004 | | |

* cited by examiner

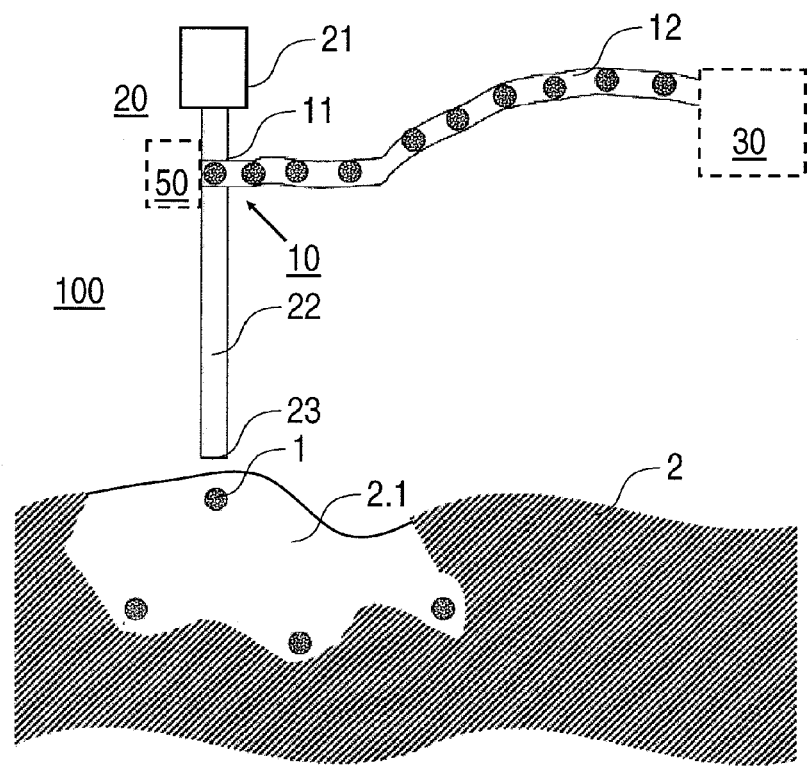
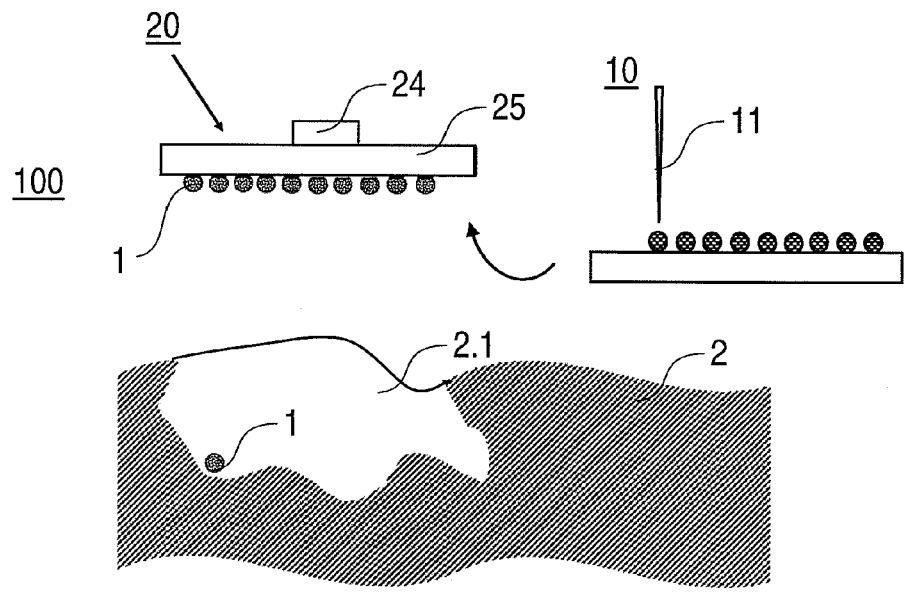
FIG. 1
FIG. 2

APPARATUS AND METHOD FOR THE DEPOSITION OF BIOLOGICAL MATERIAL IN A TARGET SUBSTRATE

BACKGROUND OF THE INVENTION

The invention relates to an apparatus which is adapted for depositing biological material in a substrate material, in particular to a deposition apparatus which is adapted for embedding biological cells or cell components in the substrate material. The invention also relates to methods for and applications of the deposition of biological material in a substrate material.

It is generally known in practice from biological or medical methods to transfer biological cells from a cell culture or donor organism to a substrate. On the substrate, the cells are subjected for example to a test or to further culturing. The substrate to which the cells are transferred may be part of a laboratory device, such as for example a culture vessel, or a biological material, such as for example a cell culture or a tissue in a biological organism. While numerous techniques (e.g. dispensing techniques, picking/spotting techniques, etc.) are available for depositing biological cells on solid substrate surfaces, the technique concerning the targeted and reproducible deposition of cells or cell components in biological material has been developed only to an insufficient extent.

In order to embed cells in the tissue of an organism for example for medical purposes, a suspension of the cells has until now been injected directly into the relevant tissue or into the bloodstream of the organism. The injection of cells into tissue, e.g. heart muscle tissue, has the disadvantage that, during the injection, the dense material of the tissue has to be displaced, with the suspended cells being subjected to high mechanical stress. Furthermore, it is disadvantageous that usually considerable volumes of liquid are introduced into the tissue during the injection, which are undesirable or cause injury to the tissue. Finally, the injection results in undefined depositions, since the distribution of the cells in the tissue can barely be influenced. Injecting the cells into the bloodstream does allow a gentle transfer into the organism; however, the problem of geometrically undefined deposition increases still further. In the bloodstream, a drifting of the cells into parts of the organism outside the target tissue may lead to undesired side effects, which may even go as far as tumor formation.

In the case of injecting stem cells or precursor cells into a cell culture or a biological organism, there are additional requirements which are met only insufficiently by conventional methods. Stem cells are extremely sensitive types of cell, the state and differentiation potential of which are influenced by mechanical and biochemical environmental conditions and particularly surface contacts. An effective therapy using stem cells, which are intended to differentiate into a specific cell type in the target tissue for example, requires a gentle transfer and a reproducible deposition in the target tissue. A locally reproducible deposition requires not only the deposition of the cells in the desired target tissue, but rather also the precise setting of the number, depth position and/or mutual spacings of the embedded cells in the target tissue.

WO 2004/074426 describes a method for the gentle transfer of biological cells into biological tissue using a transfer tool which causes displacement without causing injury. This technique may be disadvantageous in practice if large numbers of cells are to be transferred. By way of example, in regenerative medicine the task may be to introduce $10^6$ to $10^8$ cells and accordingly a suspension volume of a few milliliters into a tissue. Since the positioning of the transfer tool is extremely time-consuming, the technique described in WO 2004/074426 may be unsuitable for a routine deposition of such large numbers of cells.

EP 1637173 A2 discloses a needle-free method for introducing genetic material through skin into biological tissue. In particular, very small particles which do not damage the skin cells are to be introduced into the interior of cells. The particles are transported by a gas flow. DE 69732106 T2 also describes supplying small particles into the interior of living cells, wherein the particles are first arranged in a carrier cartridge and then are conveyed into the substrate by an air stream.

In principle, the use of frozen biological materials is known in practice from biological methods. WO 94/07603 discloses a method for cryofixing biological materials to a solid body by means of a compressed air device. Cells frozen in a cuvette are known for electroporation purposes from U.S. 2005/0214946 A1.

U.S. Pat. No. 5,219,746 A and U.S. Pat. No. 5,036,006 describe methods for transporting small particles into biological tissue by means of air pressure. Here, too, biological particles in frozen form are administered. Both methods are aimed towards transporting small particles with diameters in the range from 10 nm to a few micrometers into the interior of cells, without destroying the cells in the target substrate in the process. A transport or deposition of larger cells or of whole cell groups is thus not possible.

The abovementioned problems occur not only in the deposition of stem cells, but rather also during the introduction of other cell types, cell components or active substances when a gentle transfer without losses under predefinable geometric or quantitative conditions is necessary. By way of example, the targeted deposition of active substances, such as for example differentiation factors or growth factors, in tissue is a problem that has not yet been solved. Furthermore, said problems occur not only during the deposition of biological material in an organism, but rather also during the embedding of biological material in biological or non-biological substrate materials outside an organism, such as for example in a cell culture.

The objective of the invention is to provide an improved deposition apparatus which is adapted for depositing biological material in a target substrate and by means of which disadvantages of conventional deposition techniques are overcome. The objective of the invention is also to provide an improved method for depositing biological material in a target substrate, by means of which disadvantages of the conventional techniques are overcome.

These objectives are achieved by a deposition apparatus, an injector cartridge, a method for depositing biological material and also by a use of biological material and a use of an injector cartridge of the invention.

SUMMARY OF THE INVENTION

According to a first aspect, the invention is based on the general technical teaching of providing a deposition apparatus which is designed to deposit biological material in a target substrate and comprises a driving device, by means of which the biological material can be introduced into the target substrate by applying a driving force. The deposition apparatus is equipped with a charging device which is designed to provide the biological material at the driving device. Unlike conventional techniques for transferring biological material, the driving device is formed in such a way that the biological material in a frozen state is accelerated and at least part of the biological material is embedded in the target substrate under the effect of the driving force on the biological material.

According to a second aspect, the invention is based on the general technical teaching of providing a method for depositing biological material in a target substrate, in which the biological material is introduced in a frozen state into the target substrate under the effect of a driving force.

The inventors have found that the problems of the conventional techniques can effectively be solved by moving the biological material in the frozen state towards the target substrate at such a high speed that only the frozen biological material penetrates directly into the material of the target substrate. The route for the biological material is formed by displacement in the target substrate. The biological material in the frozen state is a solid material which comprises at least one solid particle. The solid state allows a gentle embedding of the biological material into the target substrate. Furthermore, the solid state ensures that the mass and shape of the biological material remains unchanged during the movement of the biological material towards the target substrate and during the penetration of the biological material into the target substrate. Advantageously, the deposition site and the deposition quantity can thus be set reproducibly by setting the driving force (in particular the direction and/or magnitude of the driving force). According to the invention, the biological material can be introduced into the target substrate without any encapsulation. Advantageously, the invention thus allows a residue-free embedding of the biological material in the target substrate. A significant advantage of the invention is achieved if the biological material contains at least one biological cell. In the frozen state, biological cells are not active and are not sensitive to environmental influences. Accordingly, they cannot receive any biochemical signals as they pass through the tissue during the embedding process. Advantageously, the biological material is embedded in unchanged form, i.e. the biochemical state of the biological material prior to the embedding according to the invention is identical to the biochemical state of the biological material during or immediately after deposition in the target substrate. This advantage is particularly important in the deposition of stem cells. Stem cells are characterized by the fact that, in the event of surface contacts, signal cascades can be triggered which determine the state of the cell and ultimately a differentiation of the stem cell. While in the conventional techniques in which living, non-frozen cells are introduced into tissue the cells are exposed to many biochemical signals which are undesirable or at least uncontrollable, in the method according to the invention biochemical signals during the embedding process are avoided. Only after thawing in the target substrate is it possible for contacts of the embedded stem cell with the surroundings, i.e. with biological cells in a tissue, to take place and to trigger a desired development of the stem cell.

The driving force applied by the driving device is selected as a function of the specific use of the invention in such a way that the biological material is driven at a sufficiently high speed to penetrate into the surface of the target substrate and/or to the desired depth. The speed is selected in such a way that the biological material is given a kinetic energy which is equal to the displacement work exerted by the biological material until it reaches the desired depth in the target substrate. The necessary displacement work depends on the material of the target substrate, e.g. on the type of biological tissue, and may be determined for example by simple test series. Preferably, the frozen biological material is accelerated to a speed of at least 0.5 m/s, particularly preferably at least 2 m/s. The speed is set for example by the speed of a pressurized fluid and/or of a cooling medium which acts on the biological material in the driving device.

Further advantages of the invention lie in the fact that predefined numbers of biological cells can be deposited in the target substrate. In this case, the deposited volume and/or the stress (caused by shear forces) during the deposition can be minimized. The deposition of the biological material can be carried out with a spatial resolution in the sub-millimeter range in the lateral and/or transverse direction. Without limiting the spatial deposition accuracy, the deposition apparatus (or at least part thereof) can be moved relative to the target substrate in the millimeter range or even in the centimeter range, in order to embed the biological material in a relatively large target substrate. A further advantage lies in the high deposition speed. The embedding of a large number of biological cells in a target substrate can take place within a few seconds or minutes, which is particularly advantageous for in vitro uses of the deposition according to the invention.

The embedded biological material forms a material fit with the surrounding target substrate, i.e. the embedded biological material is contacted by the material of the target substrate on all sides in the embedded state. This advantageously allows a rapid thawing after deposition and a rapid onward transport, already during the thawing process, of any cryoprotectant that may be contained in the biological material.

The term "biological material" refers here to any material which contains at least one biological cell, at least one cell group, at least one cell component, at least one biological macromolecule, such as for example enzymes, proteins, amino acids, DNA or RNA, at least one active substance (biologically or medically active additional substance) and/or at least one biocompatible additional substance, such as for example a filler, a suspension fluid or a culture medium. At room temperature or at a culturing temperature (above 0° C.), the biological material is in a liquid, flowable or deformable state. Particular preference is given to embodiments of the invention in which the biological material contains at least one biological cell, since in these embodiments the advantages of gentle embedding in the frozen state are particularly pronounced. The at least one biological cell may be for example a eukaryotic cell. The biological material contains in particular at least one of the cell types comprising stem cells, precursor cells, differentiated cells, tumor-influencing cells, nerve cells, muscle cells, particularly heart muscle cells, cartilage cells, bone cells, islet cells, gland cells, endothelial cells and epithelial cells. The at least one biological cell advantageously forms with the additional substance a composition in which the cell or cell group is surrounded by the additional substance or conversely the additional substance is surrounded by a cell group.

In the frozen state, the biological material forms at least one solid particle having a typical cross-sectional dimension of preferably less than 1 mm, particularly preferably less than 500 µm, in particular less than 100 µm, such as for example 20 µm or 10 µm or less. Typically, the mass of the particle is selected in the range from 0.1 ng to 10 µg. The small particle size gives the additional advantage of minimal wounding of the target substrate during the introduction of the biological material. In the target substrate, minimal entry channels are formed which are able to close reversibly when a deformable substrate material is used and which close after the embedding process without leaving a troublesome wound. The biocompatible additional substance optionally contained in the biological material may contain a substance which is in solid, liquid or gas form at room temperature. The biological material may be embedded for example in an inert gas, e.g. $CO_2$, which is solid in the frozen state of the biological material and transforms into the gas phase without leaving any residue after being embedded in the target substrate.

Optionally, the biological material may additionally contain a carrier material which is solid at room temperature. The carrier material comprises e.g. a substrate material, to which the biological material is connected by means of a preceding cryopreservation method.

The term "target substrate" refers here to any material composition of natural or synthetic origin which is adapted for the embedding of the biological material. The target substrate comprises in particular biological cells, e.g. as part of a human or animal organism, as part of a plant, as a cell group outside the organism or plant, or as a cell culture. As an alternative or in addition, the target substrate may comprise a solid, deformable substrate material, in particular a culture gel, such as for example agar gel, or a viscous culture fluid. If cells are contained in the target substrate, the size of the frozen particles of biological material is preferably selected to be almost equal to the size of the cells or larger.

The term "deposition" of the biological material in the target substrate refers to the embedding or introduction of the biological material into the material of the target substrate. The deposition comprises a complete embedding, in which the biological material is surrounded on all sides by the material of the target substrate, or a partial embedding, in which the biological material is embedded over at least one side in the surface of the target substrate. The introduction of the biological material is also referred to as shooting the at least one solid particle of the biological material into the target substrate. In the case of administration by means of a compressed gas for example, the frozen particle material is accelerated to a high speed and penetrates into the target substrate on account of its inertia.

The term "charging device" refers to a component which is designed to supply the biological material in a state in which it is acted upon by the driving force.

Advantageously, the deposition of biological material according to the invention can be carried out using different types of driving forces. By way of example, according to one preferred embodiment of the invention, a fluid drive may be provided which is designed to generate the driving force by applying a fluid pressure, in particular gas or liquid pressure, to the biological material. Use is advantageously made of pressure waves which are known for other technical applications, such as for example materials processing using accelerated $CO_2$ crystals or syringe-free vaccination. A further advantage of the fluid drive lies in the high effectiveness of force transmission, which allows particularly large penetration depths in the target substrate of up to 5 cm. The fluid drive comprises for example a pressure source with a controllable output valve.

The fluid drive preferably contains an acceleration line, in which the fluid flows from the pressure source. In the acceleration line, the biological material is exposed to the driving force. Advantageously, a predetermined movement direction is imposed on the biological material by the longitudinal extension of the acceleration line, so that the deposition site for the biological material can be determined by the orientation of the acceleration line relative to the target substrate.

As an alternative or in addition, according to further embodiments of the invention, a translation drive may be provided which comprises a mechanical driving element. The mechanical driving element is designed to directly apply the driving force to the biological material. The mechanical driving element preferably comprises a carrier, e.g. in the form of a plate, a rod or a grid, for holding the biological material, it being possible for the carrier to be caused to vibrate by means of a vibration source, e.g. an electromagnetic or piezoelectric vibration source. Due to the vibration, a repulsive force is applied to the biological material, under the effect of which the biological material is accelerated towards the target substrate.

The translation drive preferably contains a carrier platform which is designed to hold hanging droplets of the biological material, in particular hanging droplets of a culture medium, in which biological cells are suspended. Hanging droplets advantageously form gentle culture conditions for sensitive cells, such as for example precursor cells or stem cells. The carrier platform makes it possible to maintain the culture conditions until the point of cooling and transformation into the frozen state at the start of the deposition.

According to a preferred variant of the invention, the biological material is moved over a free distance from the deposition apparatus to the target substrate. Under the effect of the driving force, the biological material moves over a clear path, the length of which may be selected in the range from fractions of a mm to 50 cm. Particular preference is given to a clear distance having a length which is selected in the range from 1 mm to 10 cm and which is for example 0.5 cm to 2 cm. These distances have proven to be particularly advantageous for trouble-free embedding. Advantageously, the deposition site in the target substrate can also be influenced by the direction of the distance. Alternatively, the deposition apparatus may be placed on the target substrate in order to transfer the biological material.

According to a preferred embodiment of the invention, the deposition apparatus is equipped with a preparation device which is provided for preparing the biological material and supplying the latter to the charging device. Advantageously, physical and/or chemical properties of the biological material can be set immediately before the latter is transferred in the frozen state to the target substrate. Physical properties include for example the size (volume, mass) of suspension droplets and/or the number of cells contained in one suspension droplet. Chemical properties include for example the amount of cryoprotectant in the suspension droplet.

Advantageously, different variants of the invention are possible which differ with regard to the moment at which the biological material is transformed into the frozen state. Firstly, the biological material may be supplied in liquid form and may be transformed into the frozen state only at the charging device and/or during the movement towards the target substrate. In this case, the preparation device preferably comprises a droplet generator which is designed to form separate droplets of the biological material. Secondly, it may be provided according to the invention that the biological material is already transformed into the frozen state in the preparation device. In this case, the preparation device preferably comprises a particle generator which is designed to generate frozen droplets of the biological material.

This variant of the invention has the particular advantage that the biological material can no longer change after it has been prepared and supplied to the charging device. Particles may be generated for example by freezing droplets of a cell suspension which form on a hydrophobic underlayer.

In general, the deposition site for the frozen biological material can be determined by setting the driving force by means of the driving device. However, if the deposition apparatus according to the invention is equipped with a directing device which is designed to set the movement direction of the biological material, advantages may be obtained as a result of an improved deposition accuracy. The directing device preferably comprises a nozzle device with one or more outlet nozzles. Each outlet nozzle forms the end of a nozzle channel, the longitudinal direction of which determines the movement direction of the biological material. Advantageously, the nozzle device may be designed to move the biological material towards the target substrate on paths which form a predetermined geometric pattern. According to the invention, frozen particles of the biological material can be embedded simultaneously at different deposition sites in the target substrate. Advantageously, a high parallelism of the deposition for example of biological cells is thus achieved, and therefore a high deposition speed.

If the directing device forms part of a tool suitable for manual handling, advantages may be obtained with regard to a flexible orientation of the movement path of the biological material relative to the target substrate by a person operating the deposition apparatus. The directing device is preferably movable relative to the other components of the deposition apparatus. By way of example, a treating physician can orient the directing device manually like an operating tool or radiation source in a suitable manner relative to the target substrate.

According to a preferred embodiment of the invention, the charging device comprises a sample injector which is designed to supply the biological material into the driving device, in particular into the acceleration line or onto the carrier platform of the driving device. By means of the sample injector, it is possible to define the quantity of biological material that is to be embedded at a specific deposition site in the target substrate. Advantageously, use may be made of different types of sample injectors which are adapted to the respective form of biological material to be supplied to the driving device.

According to a first variant of the invention, the sample injector may comprise an injector line which opens into the acceleration line of the driving device. Through the injector line, the biological sample can be introduced into the acceleration line. The transport of the biological sample in the injector line takes place for example by means of a pressure which is applied to the charging device and/or preparation device. The injector line preferably comprises a controllable injector valve, by means of which the supply of biological material into the acceleration line can be adjusted.

According to a further variant, the sample injector comprises a droplet dispenser which is designed to supply liquid droplets of the biological material into the acceleration line or onto the carrier platform. The droplet dispenser may be constructed for example in the manner known from conventional dispenser technology for screening methods in biology or medicine. According to an alternative variant, the sample injector may comprise a particle dispenser, by means of which solid particles of the frozen biological material can be injected into the acceleration line.

Particular advantages with regard to a broad and flexible application of the deposition according to the invention are obtained if the sample injector comprises an injector cartridge which can be inserted in the acceleration line of the driving device. The injector cartridge comprises a sleeve which is designed to hold particles of frozen material. The injector cartridge comprises in the longitudinal direction an inflow opening and an outflow opening, which are designed to be flowed through by fluid of the fluid drive. As the fluid flows through the injector cartridge, the biological material is subjected to the driving force and moves with the fluid towards the target substrate. Preferably, the injector cartridge is replaceably arranged in the acceleration line. Advantageously, a charged injector cartridge can be inserted in the acceleration line and flowed through by the fluid in order to deposit the biological material. After the end of deposition, the injector cartridge can be removed from the acceleration line and replaced if necessary by a further injector cartridge.

Preferably, at least one of the inflow and outflow openings is provided with a cover element which serves to close the injector cartridge and which, when the driving force is applied, can be opened, e.g. broken through, by the flowing fluid for example. This advantageously results in an improved protection of the biological material during transport of the injector cartridge prior to insertion in the deposition apparatus.

The charging and preparation devices, which are described separately above, can alternatively be formed by a common component of the deposition apparatus according to the invention. In this case, the droplet generator for example is simultaneously used as a droplet dispenser for supplying the biological material to the driving device.

In general, the deposition apparatus according to the invention can be used without cooling. If frozen particles of the biological material are charged and deposited sufficiently quickly and if thermally insulated components are used, no cooling is required. In this embodiment of the invention, the structure of the deposition apparatus and the operation thereof are advantageously simplified. According to preferred embodiments of the invention, however, it is provided that the deposition apparatus is equipped with at least one cooling device which is designed to transform the biological material into the frozen state. Depending on the different designs of the deposition apparatus, the cooling device may be provided as an independent component or as part of the charging, preparation and/or driving device. One significant advantage of the cooling device is that the biological material can be supplied in the cooled state and/or transformed into the latter immediately before and/or during the acceleration towards the target substrate.

If, according to a first variant, the cooling device is designed to cool at least part of the charging device, advantages are obtained as a result of the biological material being transformed into the frozen state immediately before or during the process of being supplied to the driving device. If, as an alternative or in addition, the cooling device is designed to cool at least part of the driving device, further advantages can be obtained with regard to a particularly brief cooling of the biological material. The cooling device may be designed for example to supply a fluid (gas) for transmitting the driving force at a temperature below the freezing point of the biological material. In this case, the driving device advantageously fulfills the functions of cooling and driving the biological sample.

According to a further modification of the invention, the cooling device may be provided to cool at least part of the directing device, e.g. to cool the nozzle device. The functional reliability of the deposition apparatus is thus advantageously increased.

A further advantageous embodiment of the deposition apparatus according to the invention is characterized by a control circuit which is connected to the driving device. The control circuit can advantageously be used to set the driving force as a function of deposition parameters, such as for example a measured deposition site or measured particle sizes. The setting of the driving force results in an increased accuracy and reproducibility of the embedding of the biological material in the target substrate.

According to a further advantageous embodiment of the invention, the deposition apparatus is designed for switched-mode operation. The charging, driving, preparation and/or cooling devices can be switched on and off in a targeted manner. Predefined deposition protocols can thus advantageously be implemented, with which in particular the type of biological material and the associated deposition site are defined. With particular preference, the charging and driving devices are designed for synchronized switched-mode operation. The two components, in particular the injector and fluid valves, can be switched together in order to carry out a deposition of the biological material.

Further advantages with regard to the functionality of the deposition apparatus are obtained if the latter is equipped with at least one of the following additional components. By means of an imaging device, which preferably comprises at least one of a camera device, a microscopy device, an ultrasound device, a stroboscopy device and an endoscopy device, images of the deposition apparatus and/or of the target substrate can advantageously be captured. The captured images, which include for example images of the surface or of the volume of the target substrate or images of the biological material coming from the positioning device, make it possible to control the embedding of the biological material in the target substrate and/or to assess the deposition result. Furthermore, a navigation device which is designed to move and fix the deposition apparatus relative to the target substrate allows an increased deposition accuracy. Finally, a conditioning device which is designed for example to set predefined illumination and/or temperature conditions on the target substrate can be used to observe the deposition result or to influence the thawing of the biological material in the target substrate. As the conditioning device, a thawing system may be provided for example, by means of which the transformation of the biological sample into the non-frozen state in the target substrate is accelerated.

The injector cartridge of the sample injector, preferably comprising a sleeve with cover elements at the inflow and outflow openings, represents an independent subject matter of the invention.

A further independent subject matter is the use of biological material in the frozen state to modify biological tissue in a method according to the invention, wherein the biological material contains at least one cell, cell group, cell components, biological macromolecules and/or a biologically active substance.

BRIEF DESCRIPTION OF SEVERAL VIEWS OF THE DRAWINGS

Further details and advantages of the invention will be described below with reference to the appended drawings, in which:

FIG. 1: shows a schematic illustration of a first embodiment of the deposition apparatus according to the invention;

FIG. 2: shows a schematic illustration of a further embodiment of the deposition apparatus according to the invention;

DETAILED DESCRIPTION OF PREFERRED EMBODIMENTS

Figure 3:
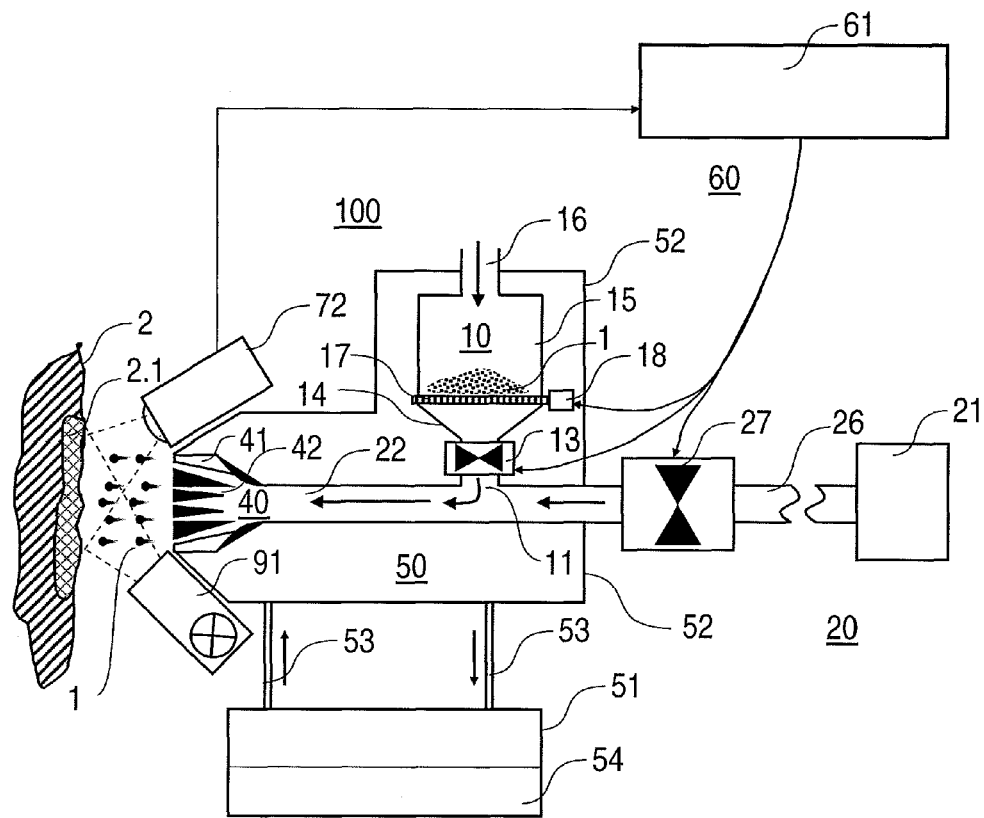
FIGS. 3 and 4: show illustrations of details of further embodiments of the deposition apparatus according to the invention.

The invention will be described below firstly with reference by way of example to the embedding of biological cells in a biological tissue inside or outside a biological organism. However, the invention is not restricted to this application. The embedding of biological materials in the volume or surface of other target substrates, such as for example cell cultures, can be carried out in a corresponding manner. Details regarding the transformation of biological materials into the frozen state, such as for example details concerning the cooling medium used, the addition of a cryoprotectant or the steps of the freezing method, will not be explained below since they are known per se from the conventional cryopreservation of biological samples.

FIG. 1 shows a first embodiment of a deposition apparatus 100 according to the invention in a schematic sectional view. The deposition apparatus 100 comprises a charging device 10 with a sample injector 11 and an injector line 12, and a driving device 20 with a pressure source 21 and an acceleration line 22. As optional components, a preparation device 30 and a cooling device 50 are additionally shown.

The sample injector 11 is formed in the simplest case by the mouth of the injector line 12 into the acceleration line 22. Droplets or frozen particles of the biological material 1 are transported through the injector line 12 under the effect of a pressure from the preparation device 30 to the sample injector 11. The injector line 12 is a tube or hose, e.g. made from glass or plastic, with an internal diameter of for example 0.2 mm. Transported in the injector line 12 are e.g. liquid suspension droplets, between which gaps are formed by air or inert gas. Alternatively, frozen droplets may be transported in the acceleration line 12. In this case, the acceleration line is preferably made from a low-friction plastic material, such as PTFE for example.

The pressure source 21 is a pressurized gas source which contains an inert gas, such as nitrogen for example, and is equipped with a controllable fluid pressure valve (see FIG. 3). The acceleration line 22 is a hollow line, for example in the form of a tube or hose, which is connected at one end to the pressure source 21 and has a second, free end with an outlet opening 23. The acceleration line 22 is preferably formed in a straight line at least at the end pointing towards the outlet opening 23, but preferably is completely straight. It is made for example from glass or dimensionally stable plastic with an internal diameter of for example 100 pm and a length of for example 3 cm. For a free orientation of the acceleration line 22 in space, a flexible hose connection to the pressure source 21 may be provided, said pressure source being arranged in a stationary manner. Furthermore, for manual handling of the deposition apparatus 100, a handle (not shown) may be provided on the outer side of the acceleration line 22.

The preparation device 30 comprises a droplet or particle generator, by means of which the droplets or particles in the injector line 12 are generated. The droplet generator consists for example of a pump which conveys predefined droplet volumes from a storage vessel containing a cell suspension into the injection line 12.

The cooling device 50 is shown by way of example at the location of the sample injector 11. As an alternative or in addition, the cooling device 50 may be integrated in the preparation device 30 or in the driving device 20, specifically in the pressure source 21.

The target substrate 2 illustrated by way of example in FIG. 1 comprises a wound region 2.1 within a muscle tissue. The aim of the deposition of the biological material 1 according to the invention is to embed epithelial cells or precursor cells of epithelial cells in the wound region 2.1, in order to promote wound healing.

In order to deposit the biological material 1 in the wound region 2.1, the biological material 1 introduced into the driving device 20 by the charging device 10 is subjected to the driving force which is applied to the biological material 1 by the gas flowing through the acceleration line 22 from the pressure source 21. Under the effect of the driving force, the biological material 1 in the frozen state moves through the acceleration line 22 firstly between the outlet opening 23 and the wound region 2.1 on a clear flight path. When it reaches the surface of the wound region 2.1, the biological material 1 can penetrate the cells of the wound region 2.1 on account of its kinetic energy and can be embedded at the desired deposition depth.

The embodiment of the deposition apparatus 100 shown in FIG. 1 can be modified to the effect that the charging device comprises a combination of an injector line 12 and a feed funnel (see FIG. 3). Frozen particles of the biological material are filled into the feed funnel and are moved from the latter under the effect of gravity to the sample injector 11, in order to be acted upon in the acceleration line 22 by the driving force applied by the flowing gas from the pressure source 21.

In the embodiment of the deposition apparatus 100 according to the invention shown in FIG. 2, the driving device 20 forms a mechanical translation drive with a driving element 24 and a vibrating carrier platform 25. A component separate from the driving device 20 is provided as the charging device 10, which is designed to deposit droplets of the biological material 1 on the carrier platform. In this case, a pipette or another droplet dispenser is used as the sample injector 11. The biological material 1 is provided at the driving device 20 in the manner known per se from the conventional culture of hanging droplets. Firstly, the droplets of the biological material 1 are placed on the carrier platform 25. The carrier platform 25 is then turned over by a rapid pivoting movement, so that the suspension droplets are transformed into the hanging state. In this situation, firstly a culturing of cells in the hanging droplets may be provided, for example in order to form cell groups in each droplet before embedding the biological material 1 in the target substrate 2. As the target substrate 2, there is provided for example in a manner analogous to FIG. 1 tissue containing a wound region 2.1, in which biological material 1 containing epithelium-forming cells is to be embedded.

The deposition according to the invention of the biological material 1 in the target substrate 2 comprises applying to the biological material 1 the mechanical driving force which is generated by the translation element 24 and is transmitted by the carrier platform 25 to the biological material 1, for example as a result of vibrations.

The movement of the biological material in a frozen state into the target substrate 2 then takes place. Depending on the specific use of the invention, the transformation of the biological material 1 into the frozen state may already take place while the biological material 1 is still located on the carrier platform 25. As an alternative or in addition, a freezing may be provided along the route from the carrier platform 25 to the target substrate 2. In both cases, the freezing takes place by blowing of vapor of liquid nitrogen, which has a temperature of −130° C.

In the embodiment of the deposition apparatus 100 according to the invention which is shown in FIG. 3, the charging device 10 comprises as the sample injector 11 a dropping opening, through which frozen particles of the biological material 1 fall from a feed funnel 14 into the acceleration line 22 of the driving device 20 when the injector valve 13 is actuated.

The charging device also contains a storage container 15 which receives via an opening 16 the already frozen biological material 1. The biological material 1 can be supplied via the opening 16 once, periodically or continuously by a preparation device (not shown), by means of which the frozen particles of the biological material 1 are generated. The transfer of the biological material 1 from the storage container 15 to the feed funnel 14 takes place via a sieve 17. By moving the sieve 17 by means of a vibrating element 18, e.g. by shaking or vibration, it is possible to influence the throughput from the storage container 15 to the feed funnel 14.

The pressure source 21 of the driving device 20 is connected to the acceleration line 22 via a pressure line 26 in the form of a flexible hose and a fluid pressure valve 27. At the end of the acceleration line 22, the directing device 40 is provided with a nozzle arrangement 41, at which the channel of the acceleration line 22 splits into a plurality of individual nozzle channels 42. The nozzle openings of the nozzle channels 42 form a predetermined geometric pattern. The nozzle arrangement 41 is preferably releasably attached to the acceleration line 22 and is replaceable. This makes it possible to use a suitable nozzle arrangement 41 with an appropriate number of nozzle channels 42 and an appropriate pattern of the nozzle openings, depending on the requirements of a specific use.

In the embodiment of the deposition apparatus according to the invention which is shown in FIG. 3, the cooling device 50 is designed to cool the charging device 10, part of the driving device 20 and the directing device 40. The cooling device 50 comprises a coolant reservoir 51 and a cooling container 52, which are connected to one another via hoses 53. The coolant reservoir 51 is designed to hold a liquid coolant 54 (e.g. liquid nitrogen). For the cooling mode, a circulation of the vapor of the liquid nitrogen via the hoses 53 is provided (see arrow) between the coolant reservoir 51 and the cooling container 52. The coolant reservoir 51 forms a cryostat. A temperature in the range from −20° C. to −150° C. is provided for example in the cooling container 52. The components of the cooling device 50 are made from thermally insulating materials which are known per se.

FIG. 3 illustrates an optionally provided control circuit 60 comprising a control device 61 which is designed to actuate the injector valve 13, the fluid pressure valve 27 and/or the vibrating element 18 as a function of at least one deposition reference value. The deposition reference value is derived for example from the measurement signal of a microscope device 72 or another imaging or monitoring device and is characteristic of an operating state of the deposition apparatus 100. If, for example, in a given operating state the quantity and/or the penetration depth of the biological material 1 in the target substrate 2 does not correspond to the desired parameters, the control circuit 60 can be used to adjust at least one of the parts 13, 27 and 18 in order to increase or reduce the number of supplied particles of the biological material 1 and/or to increase or reduce the driving force applied by the driving device 20.

FIG. 3 illustrates as a further component the illumination device 91 which is designed to illuminate the target substrate 2 and contains for example a white light source or a laser source. The illumination device 91 and the microscope device 72 can be fixedly connected to the other components of the deposition apparatus 100 and may be attached for example to the outside of the cooling container 52.

Instead of the microscopy device 72, a different imaging instrument may be provided, such as for example an ultrasound device or a tomography device.

In order to carry out the deposition method according to the invention, the deposition apparatus 100 is oriented relative to the target substrate 2, in particular relative to a wound region 2.1 that is to be treated. After the topography of the wound region 2.1 has been detected by means of the microscope device 72, a fine adjustment of the directing device 40 may be provided if necessary. After the adjustment, the biological material 1 in the form of frozen particles is introduced via the feed funnel 14 and the injector valve 13 into the acceleration line 22, through which air or nitrogen flows. To this end, the valves 13 and 27 are opened and the vibrating element 18 is actuated. The frozen particles of the biological material 1 exit through the directing device 40 on clear movement paths which lead towards the wound region 2.1. Depending on the observed deposition result, the supply of biological material is continued, interrupted or modified for example relative to the type of biological material.

Figure 4:
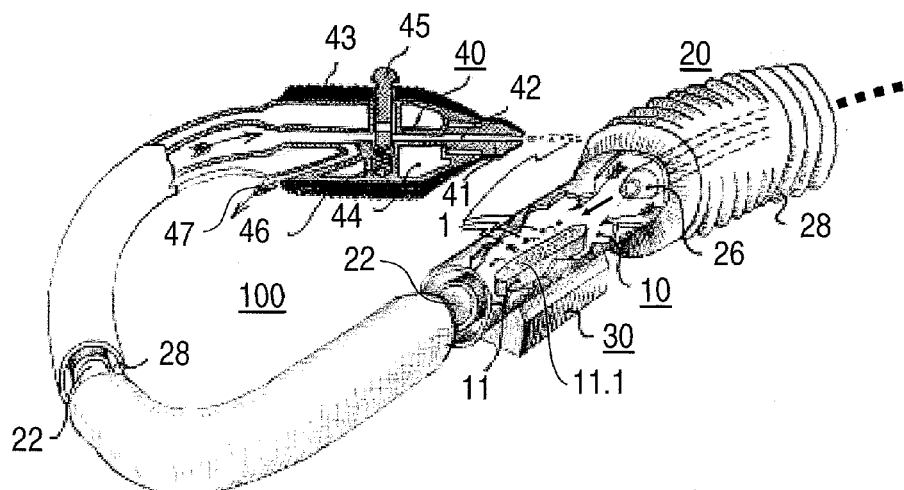

FIG. 4 shows a modified embodiment of the deposition apparatus 100 according to the invention, which is characterized by a compact design and the suitability for manual handling. For illustration purposes, the deposition apparatus 100 in FIG. 4 is shown partially in a perspective phantom view and partially in a sectional view.

The deposition apparatus 100 has an elongate, hose-like structure which extends from the driving device 20 via the charging device 10 with the preparation device 30 to the directing device 40. Provided in the deposition apparatus 100 are at least two chambers which extend along the hose shape and which hold firstly the accelerating fluid for transmitting the driving force to the biological material and secondly a coolant for cooling the biological material and transforming it into the frozen state. The chambers form for example coaxially arranged gas and/or liquid lines.

The driving device 20 comprises a coaxial structure with an inner pressure line 26 and an outer coolant line 28, which are respectively connected to a pressure source and a coolant reservoir (both not shown). The two lines are equipped with controllable valves. The inner pressure line 26 consists for example of a plastic hose, which is positioned in the outer coolant line 28 by means of spacers. The outer coolant line 28 consists of a flexible hose which is constructed with an insulating material, e.g. a metal bellows-type hose with an insulating plastic coating.

The charging device 10 comprises a chamber which is designed to be flowed through by the central flow of pressurized fluid and the outer flow of coolant. As the sample injector 11, there is provided a droplet dispenser comprising at least one dispenser nozzle 11.1 which protrudes into the central pressurized fluid flow. In the illustrated embodiment, the droplet dispenser comprises a plurality of dispenser nozzles 11.1 which are arranged as a row in the flow direction of the pressurized fluid flow (see arrow), so that advantageously a plurality of droplets of the biological material 1 can be injected simultaneously into the pressurized fluid flow. The sample injector 11 protrudes through the outer coolant flow into the central pressurized fluid flow, so that the biological material is first injected in liquid form into the pressurized fluid flow. The sample injector 11 is connected to the schematically shown preparation device 30, which contains a sample reservoir and a pump for conveying a suspension or solution of the biological material to the sample injector 11.

The acceleration line 22, which is surrounded coaxially by a second section of the coolant line 28, extends downstream from the charging device 10 until it reaches the directing device 40. During the movement of the biological material 1 in the pressurized fluid flow through the acceleration line 22, a cooling of the biological material to below its freezing point takes place as a result of a heat exchange with the coolant flow in the coolant line 28, so that the biological material is in the frozen state at the latest by the time it passes through the directing device 40. The length of the acceleration line 22 from the charging device 10 to the directing device 40 is for example 4 cm to 5 m.

The directing device 40 comprises a nozzle arrangement 41 with a nozzle channel 42, a handpiece 43, cooling chambers 44, an actuating device 45, 46 and an outflow channel 47. The handpiece 43 forms a hollow cylinder made from a thermally insulating plastic material, in which the components 44 to 47 are arranged and which tapers conically in the downstream direction towards the nozzle arrangement 41. The cooling chambers 44 are designed to hold the coolant flowing through the coolant line 28 and to further set or maintain the frozen state of the biological material 1. Given a sufficient thermal insulation of the handpiece 43 and a sufficient length of the acceleration line 22, the cooling chambers 44 can be omitted.

The actuating device comprises a valve plunger 45, the free end of which protrudes out of the handpiece 43, and a spring 46, by means of which the valve plunger 45 is spring-mounted. By way of example it is provided that, in the state in which no pressure is exerted, the acceleration line 22 is closed and is separated from the nozzle channel 42. By exerting a mechanical pressure on the valve plunger 45, e.g. using a finger, a through-opening in the valve plunger 45 is aligned with the acceleration line 22, so that the connection to the nozzle channel 42 is enabled. Preferably, the actuating device 45, 46 is additionally equipped with a switch (not shown), by means of which the sample injector 11 and one of the valves in the lines 26, 28 can be actuated.

The overflow line 47 serves for branching coolant from the coolant line 28 and the cooling chambers 44. For safety reasons, the overflow line 47 is arranged in such a way that the hand of a person holding the directing device 40 is not struck by the escaping coolant.

In order to carry out the deposition method according to the invention, coolant in gas or liquid form, e.g. liquid nitrogen, flows at a predetermined coolant temperature through the coolant line 28 from the driving device 20 via the charging device 10 to the directing device 40. By means of the pressurized fluid line, a pressurized fluid flow, e.g. of nitrogen or air, is conducted through the charging device 10 and the acceleration line 22 to the directing device 40. By means of the sample injector 11, droplet-type samples of biological material 1 are injected into the pressurized gas stream and are transported downstream with the latter through the acceleration line 22. The injection of the droplets takes place by means of gas pulses or by means of a piezoelectric droplet generator. On the route through the acceleration line 22, the biological material 1 is transformed into the frozen state. Through the nozzle channel 42, the biological material 1 exits on a clear movement path towards a target substrate (not shown).

The embodiment of the deposition apparatus 100 shown in FIG. 4 can be modified in such a way that the function of cooling the biological material is performed by the pressurized gas stream. In this case, the coaxial structure can be replaced by a single thermally insulated line. As the pressurized gas, use is made for example of pressurized vapor of liquid nitrogen. In this case, a freezing of the droplets of the biological material 1 takes place immediately after exiting from the sample injector 11. Furthermore, it is possible in this case to omit the coaxial structure of the acceleration line 22 with the coolant line 28. The coolant line 28 can be replaced by an evacuated chamber which surrounds the acceleration line 22. Furthermore, the nozzle arrangement 41 comprising a single nozzle channel 42 can be replaced by a structure comprising a plurality of nozzle channels, as shown for example in FIG. 3. The deposition apparatus 100 shown in FIG. 4 may be equipped with further components, e.g. for monitoring the deposition apparatus and/or for imaging the target substrate.

Figure 5:
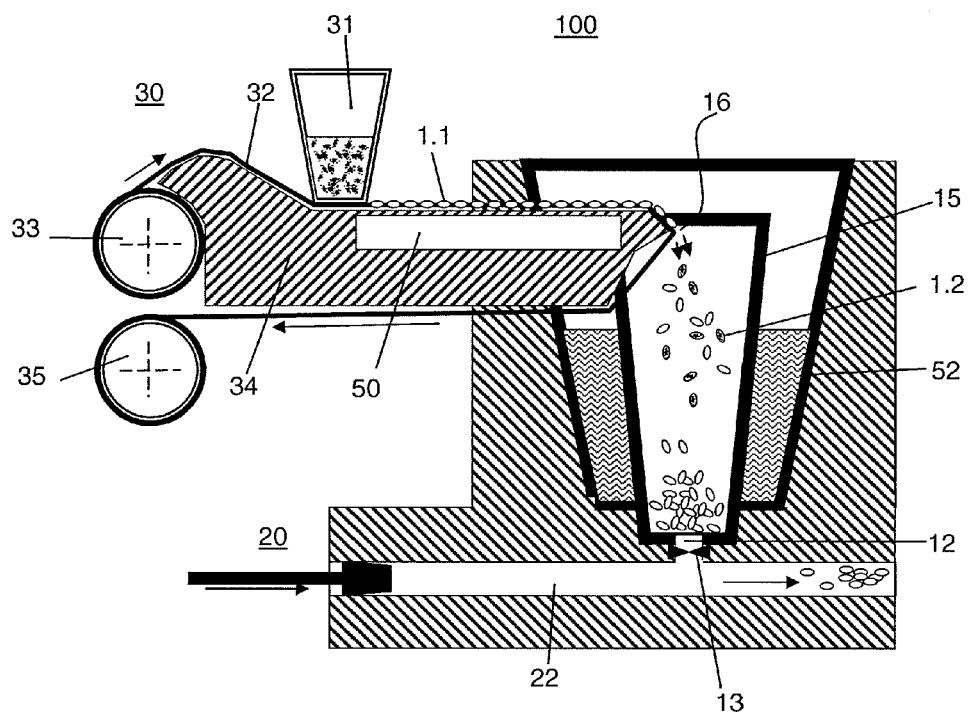
FIG. 5: shows a schematic illustration of a further embodiment of the deposition apparatus according to the invention.

FIG. 5 shows a further embodiment of a deposition apparatus 100 according to the invention in a schematic sectional view. The deposition apparatus 100 comprises a preparation device 30, by means of which the frozen particles 1 that are to be shot are generated from a cell suspension directly before shooting. From a storage vessel 31, the cell suspension passes onto a conveyor belt 32 running therebelow. The conveyor belt 32 runs from an inlet drum 33 over a body 34 below the storage vessel 31 and in the process picks up cell suspension. The conveyor belt 32 is preferably hydrophobic at least on the surface or completely, so that the cell suspension forms individual droplets 1.1 thereon. From the storage vessel 31, the droplets 1.1 are then transported over the body 34, which is made here from PTFE for example, and over a cooling device 50 in the form of a cooling plate to the opening 16 of a storage container 15. In the process, the droplets 1.1 are frozen to temperatures below −30° C. and thus form frozen particles 1.2. In the opening 16 of the storage container, the conveyor belt 32 runs over an edge, whereby it is greatly deformed. As a result of the bending stress which occurs in the process, the frozen particles 1.2 drop from the conveyor belt 32 and thus pass into the storage container 15 for the frozen particles 1.2.

The storage container 15 is surrounded by a coolant container 52 filled with coolant. As the coolant, use is made for example of liquid nitrogen. The entire system is preferably thermally insulated. From the storage container 15, the frozen particles (crystals) 1.2 pass for example as a result of gravity into an injector line 12. Through the injector line and a closable injector valve 13, the particles 1.2 finally pass to a driving device 20, from where they can be shot directly. They preferably pass directly through the injector valve into an acceleration line 22 of the driving device 20.

Via the rotation of an uptake roller 35, the speed of the conveyor belt 32 can be controlled. With an additional control of the cooling plate 50, it is possible to control the freezing process so that temperature programs can be carried out in a targeted manner. This allows the use of optimal temperature programs for the cryopreservation of the respective cells or other biological materials. Moreover, with this arrangement, the quantity of particles to be shot can be freely selected.

Figure 6:
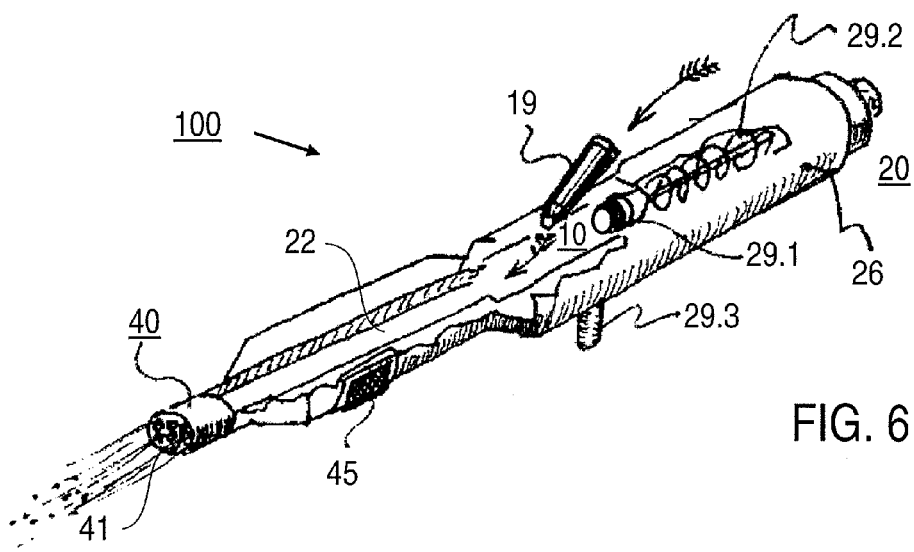
FIGS. 6 and 7: show details of the use of a first variant of the injector cartridge according to the invention.
Figure 7:
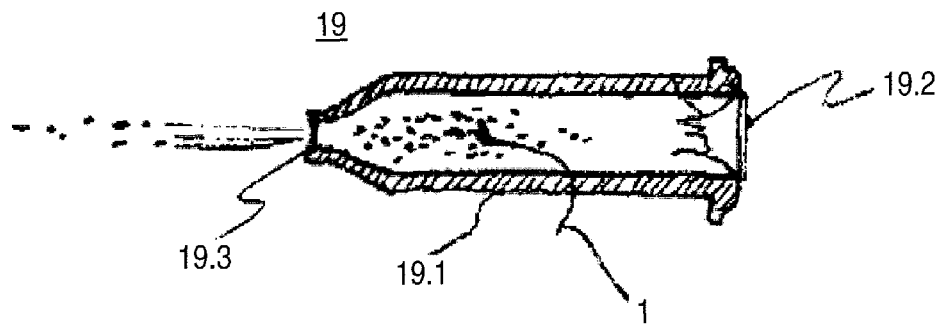

FIGS. 6 and 7 illustrate a further embodiment of the deposition apparatus 100 according to the invention, in which the charging device 10 is provided with an injector cartridge 19. In this embodiment, the driving device 20 comprises an elongate housing, the rear and front parts of which accordingly form the pressure line 26 and the acceleration line 22 and at the downstream front end of which there is arranged the directing device 40 with the nozzle device 41.

The charging device 10 comprises a chamber between the pressure and acceleration lines 26, 22. This chamber is designed to hold the injector cartridge 19. The injector cartridge 19 comprises a cartridge sleeve 19.1 made from a thermally insulating plastic (FIG. 7). The cartridge sleeve 19.1 has in the longitudinal direction an inflow opening and an outflow opening, which are accordingly closed by cover elements 19.2, 19.3. By means of the cover elements 19.2, 19.3, the interior of the cartridge sleeve 19.1 is closed during the storage thereof. When the cover elements 19.2, 19.3 are subjected to a fluid pressure of the driving device 20, the cover elements 19.2, 19.3 are opened so that the pressurized fluid flow can pass through the injector cartridge 19 and can transport the biological material 1 through the acceleration line 22 and the directing device 40 to the target tissue (not shown).

The injector cartridge 19, which represents an independent subject matter of the invention, contains the biological material 1 in the frozen state. Advantageously, the injector cartridge 19 can be filled with the frozen material 1, stored and transported independently of the operation of the deposition apparatus 100.

The injector cartridge 19 is held in the charging device 10 by a clamping device which is arranged in the pressurized fluid line 26 and comprises a retaining ring 29.1, a clamping spring 29.2 and a clamping lever 29.3. In order to insert the injector cartridge 19 through a lateral opening of the housing of the deposition apparatus 100, the retaining ring 29.1 is pulled back using the clamping lever 29.3 and is released once the injector cartridge 19 has been inserted. The retaining ring 29.1 is seated against the rear edge of the cartridge sleeve 19.1 and leaves the cover element 19.2 exposed for the application of the fluid pressure of the driving device 20.

In order to carry out the method according to the invention, a filled, cooled injector cartridge 19 is inserted into the charging device 10. The deposition apparatus 100 is then positioned relative to the target substrate. By means of an actuating button 45, a pressurized fluid valve in the pressure line 26 is opened, so that the pressurized fluid flows at high speed through the pressure line 26, breaks through the cover elements 19.2, 19.3 of the injector cartridge 19 and entrains the biological material through the acceleration line 22.

Figure 8:
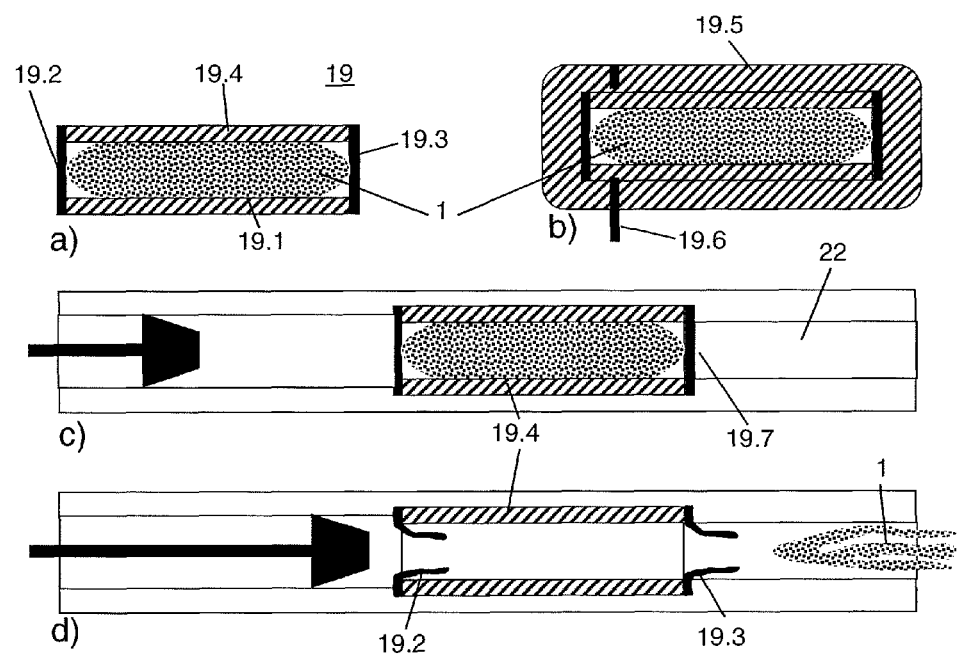
FIG. 8: shows a schematic diagram of the use of a second embodiment of the injector cartridge according to the invention.

FIGS. 8a to 8d show an alternative embodiment of an injector cartridge 19 and the use thereof. FIG. 8a shows the cartridge 19 in a sectional view with a thermally insulating casing 19.4, which internally by means of a pressurized sleeve 19.1 surrounds the interior containing the frozen particles 1.

The sleeve 19.1 has an inflow opening and an outflow opening, which are both respectively closed by a thin membrane 19.2, 19.3, for example made from plastic, cellulose or metal. For storage or transport, the injector cartridge 19 is located in an additional thermally insulating transport casing 19.5. The transport casing 19.5 has a tear-off strip 19.6 which, when torn off, can be separated into two parts which are then removed from the injector cartridge for example towards the front and towards the rear (FIG. 8b).

For use in a deposition apparatus, the injector cartridge 19 without the transport casing 19.5 is inserted into a cartridge holder in the acceleration line 22 (see e.g. FIG. 6). The position of the injector cartridge 19 in the acceleration line 22 is secured in such a way that it cannot be displaced in the direction of the outflow side when pressure is generated from the inflow side. This is achieved for example by the fact that the internal diameter of the acceleration line 22 on the outflow side 19.7 of the injector cartridge 19 is smaller than the external diameter of the casing 19.4 (FIG. 8c). In order to shoot the frozen particles 1, the membranes 19.2 and 19.3 are broken by a brief significant rise in pressure or else mechanically. The frozen particles 1 then leave the cartridge 19 and the acceleration line 22 in the direction of the outflow opening (to the right in FIG. 8d).

As an alternative, the sleeve 19.1 may be closed on the inflow side by a deformable membrane 19.2 which is not broken by the shooting process but rather merely transmits the pulse. In this case, only the membrane 19.3 on the outflow side is broken.

FIGS. 9A to 9L show different variants of the shape and composition of the biological material 1, which according to the invention is embedded in the frozen state in the target substrate, in enlarged, schematic cross-sectional views. The cross-sectional dimension of the frozen particles of the biological material is typically selected in the range from 3 μm to 5 mm, preferably in the range from 20 μm to 5 mm. The particles typically have a volume in the range from 25 μm$^3$ to 20 mm$^3$. Preferably, the biological material 1 comprises at least one biological cell 3 or cell group 5, for example of eukaryotic cells, and at least one additional substance 4. The additional substance 4 is typically the surrounding medium in which the cell was prepared for the deposition. Alternatively, the biological material may consist exclusively of the additional substance supplied in the frozen state, such as for example a filler, a suspension fluid, or a culture medium.

Figure 9:
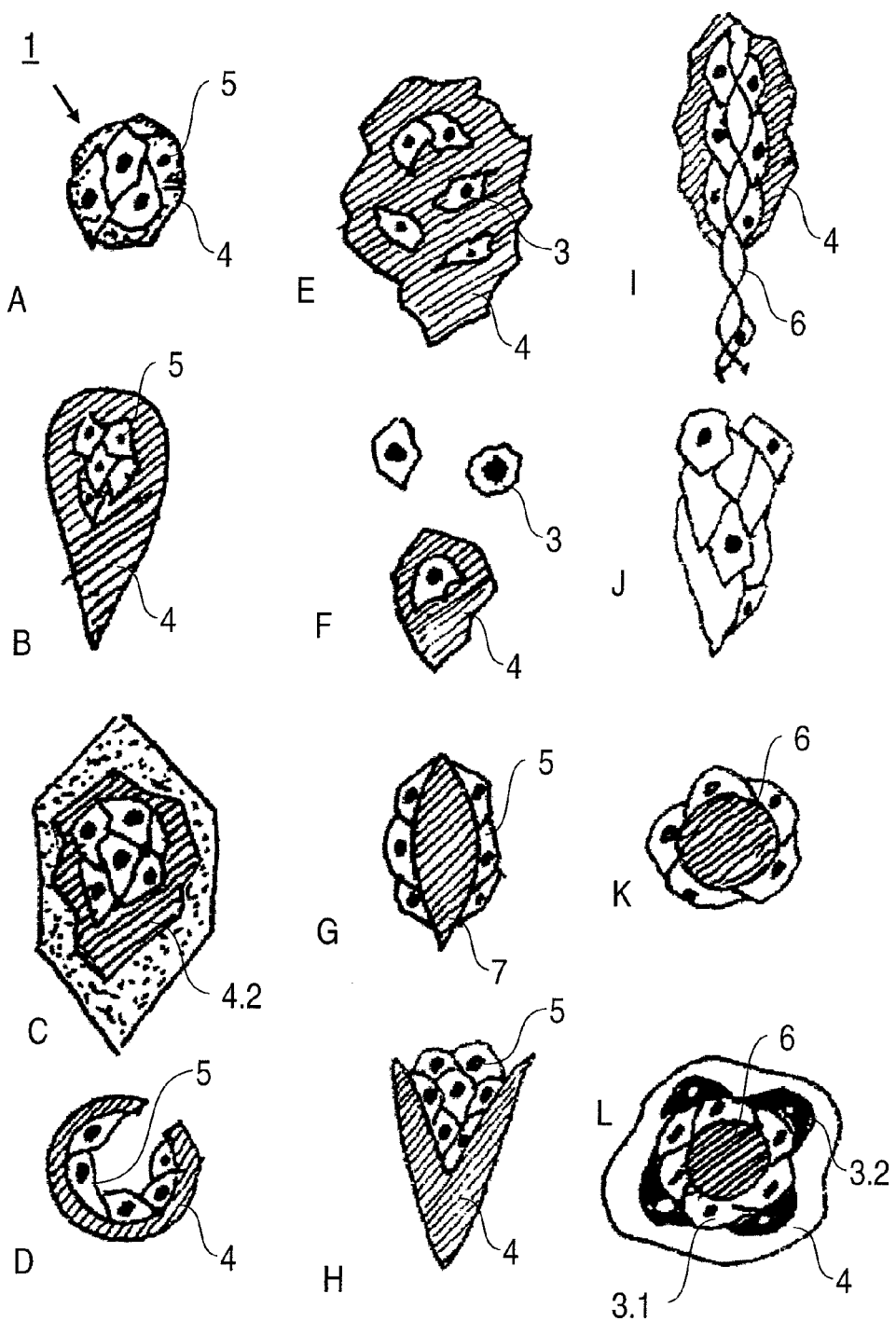
FIG. 9: shows illustrations of different variants of biological material which is used according to the invention for embedding in a target substrate.

In FIG. 9A, the biological material comprises a composition containing the cell group 5 and the additional substance 4. The additional substance 4 has a negligible volume compared to the cell group 5. It is advantageous to reduce the additional substance 4 to a minimum (frozen residue of a surrounding solution) if the cells are to be introduced into the target substrate with minimal displacement and the lowest possible contamination, as is of interest in particular in applications in medicine and tissue engineering.

As an alternative, as shown in FIG. 9B, the biological material may comprise the cell group 5 and the additional substance 4, the volume of which is equal to or greater than the volume of the cell group 5. This variant has the advantage that a defined quantity of a predetermined solution, which may for example contain active substances, can be introduced with the cells into the target substrate. Furthermore, the encapsulation by the frozen additional substance 4 offers improved protection during the embedding of the cell group 5 in the target substrate. Finally, a large volume of the additional substance 4 facilitates the possibility of forming the frozen particles of the biological material with a predetermined shape. During the freezing process for example, a particle shape consisting of an elongate ellipsoid may be formed, which facilitates penetration into the target substrate. Furthermore, the position of the particle in the target substrate can be influenced by the shaping.

According to the invention, the biological material may contain a plurality of additional substances 4.1, 4.2, as shown by way of example in FIG. 9C. The cell group 5 is surrounded by a plurality of layers of encapsulating solutions in the frozen state. By way of example, the inner additional substance 4.1 comprises a culture medium with a cryoprotectant, and the outer additional substance 4.2 comprises a culture medium without a cryoprotectant. Such a multilayer structure can be generated by firstly freezing for example the cell group with the inner additional substance and then coating it with the outer additional substance by dipping. The advantage of this embodiment of the invention is obtained when thawing the biological material in the target substrate. Upon thawing, the two additional substances 4.1, 4.2 mix together, so that the concentration of the cryoprotectant in the total volume of the two additional substances decreases. Advantageously, therefore, an increased survival rate of the embedded cells is achieved due to reduced stress when thawing.

According to a further variant (FIG. 9D), the additional substance 4 may form a hollow body, in particular a hollow sphere. In this case, it may be advantageous that the cell group 5 has a free cell surface and nevertheless is protected by the additional substance 4 during the embedding in the target substrate. The hollow body of the additional substance 4 shown in FIG. 9D may be formed by a frozen liquid or a frozen gel or, according to a further variant of the invention, by a solid carrier material (see also FIG. 9G).

Alternatively, the biological material may be formed of a composition consisting of a plurality of individual cells 3 and the additional substance 4 (see FIG. 9E). In applications in tissue engineering or in cell cloning, it is advantageous if, as shown in FIG. 9F, individual cells are embedded without or with an additional substance 4 in the target substrate.

As shown in FIG. 9G, the additional substance may form, e.g. as a frozen liquid or frozen gel (or alternatively as a solid carrier material 6), a carrier for the cell group 5. In this case, advantageously a high mechanical stability of the frozen particle and a direct contact of the cells 5 with the target substrate is achieved.

FIG. 9H shows a further embodiment of a composition used according to the invention which consists of a cell group 5 with an additional substance 4 which forms a protective cavity for the cell group 5.

A further variant of a composition comprising a solid carrier material 6 is shown in FIG. 9I. The carrier material 6 comprises a substrate, on which biological cells 3 are grown or adhered. The substrate comprises for example a tissue, a fiber, a mesh, a gel, a polymer or the like. The solid carrier material 6, optionally in conjunction with the additional substance 4 in the frozen state, advantageously forms a solid body which can be shot into the target substrate in the same way as the other illustrated frozen particles. In a manner differing from the variant shown in FIG. 9I, the biological material may be formed without the additional substance 4, i.e. exclusively with the biological cells 3 and the solid carrier material 6.

According to the invention, the biological material may be a conglomerate (agglomeration, mixture) of different frozen parts which do or do not contain cells. One example of such a conglomerate particle is shown schematically in FIG. 9J. Conglomerates have the advantage that the individual parts can be combined as required and, after reaching the target substrate or after thawing, break down and are separately active.

A further example of a biological material with a solid carrier material 6 is shown in FIG. 9K. In this case, the solid carrier material 6 forms a core body which may for example contain substances which are not released until after the embedding and thawing of the biological material. Advantageously, therefore, the active region of the substances is limited to the deposition site. The solid carrier material 6 may be a spherical solid (bead), a gel, a polymer or a frozen liquid particle.

The above-described variants of the composition of the biological material can be combined and extended, as illustrated by way of example in FIG. 9L. For example, a plurality of cell types 3.1, 3.2 may be arranged on a central carrier material 6 and surrounded by an external additional substance 4. Advantageously, pre-prepared tissue particles, e.g. islet cells encapsulated by alginate, can thus be embedded in the target substrate in the form of xeno-transplants or for allogenic transfer.

Figure 10:
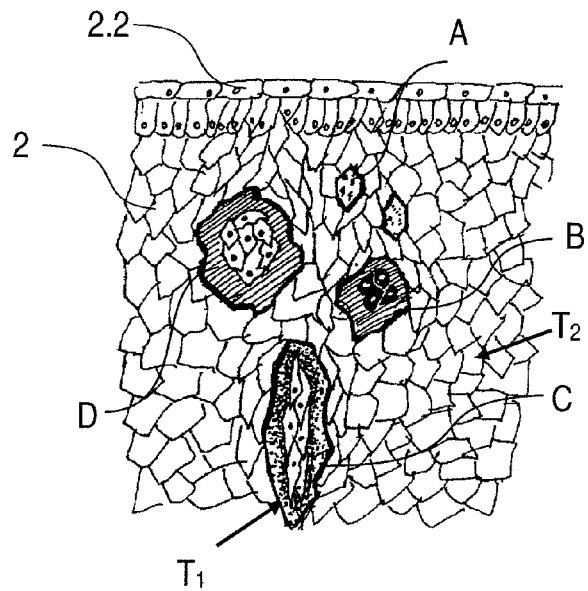
FIG. 10: shows a schematic cross-sectional view of a target substrate with embedded biological material.
Figure 11:
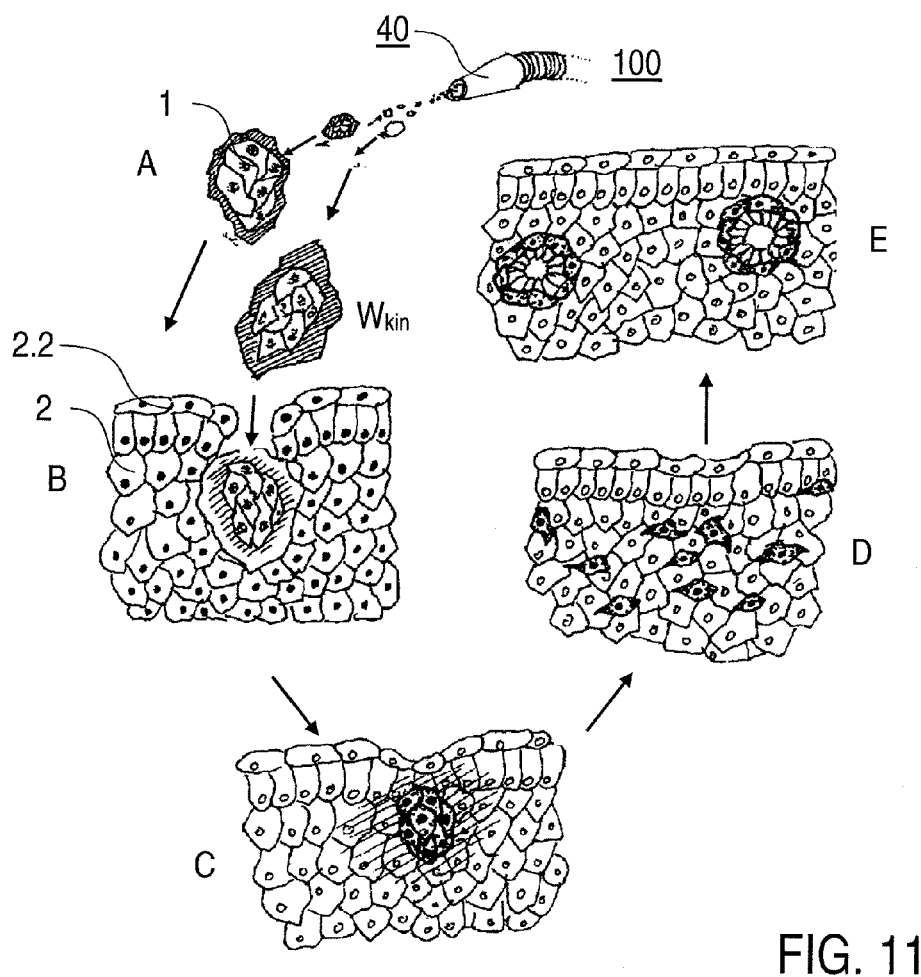
FIG. 11: shows cross-sectional illustrations of different phases of the embedding of biological material in the target substrate.
Figure 12:
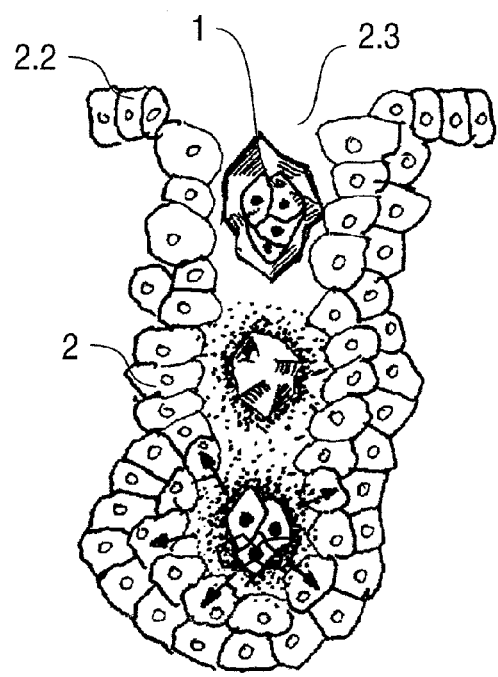
FIGS. 12 to 15: show illustrations of further features of preferred embodiments of the deposition method according to the invention.
Figure 13:
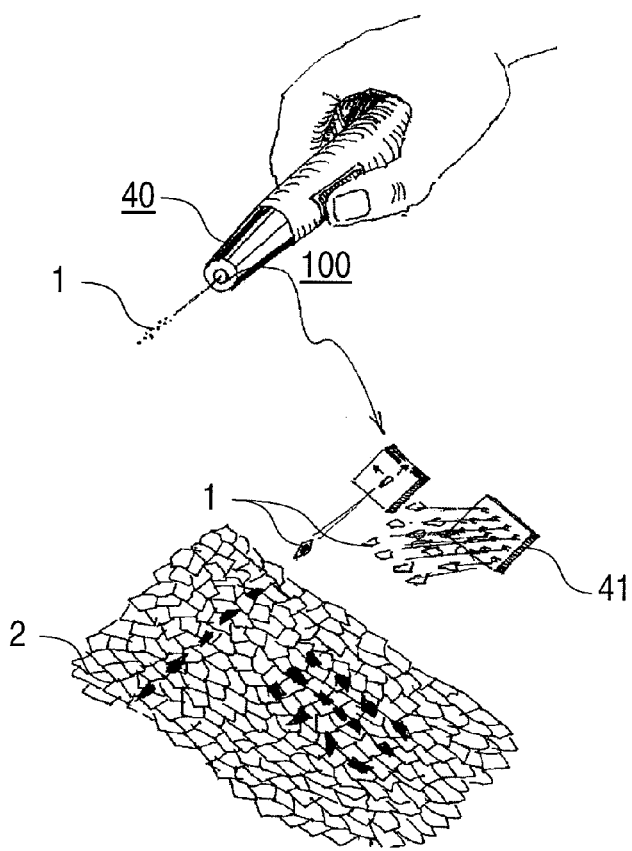
Figure 14:
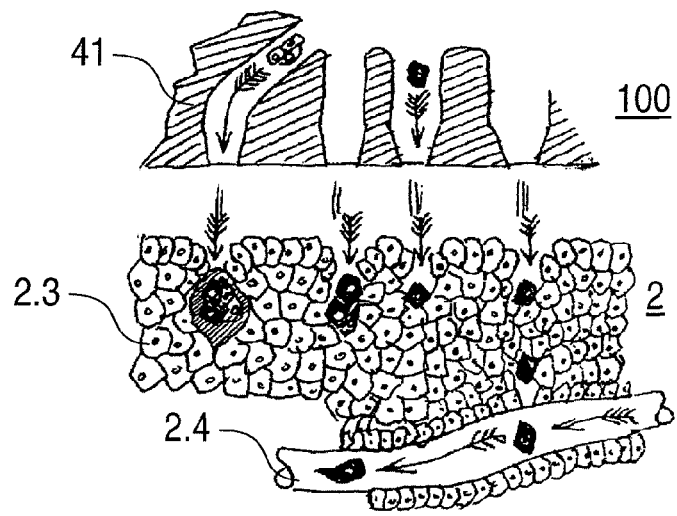

FIG. 10 illustrates in a schematic sectional view different types of embedded particles of frozen material in a target substrate 2, which is formed by a tissue of biological cells. The particles A, B, C and D are embedded in the frozen state at a first temperature $T_1$ in the target substrate 2, which is at an ambient temperature $T_2$. Depending on the materials used and the specific application of the invention, the temperature $T_1$ may be selected in the range between for example −270° C. and the freezing point of the particle, preferably in the range from −40° C. to −160° C. Temperatures below −130° C. are particularly advantageous, since in this temperature range for example $CO_2$ is stable and ice crystals do not exhibit any migratory growth. The temperature $T_1$ may moreover be selected to achieve a predetermined penetration depth in the target substrate 2. Since, during the embedding of the biological material in the target substrate 2, the particles are heated due to frictional heat and heat exchange with the target substrate 2, the penetration depth of the biological material 1 in the target substrate 2 can be set by the choice of temperature $T_1$, taking account of the size of the frozen particles. The ambient temperature $T_2$ is typically the room temperature, a culturing temperature or the tissue temperature of the living organism (e.g. 36° C. to 37° C. in humans).

FIG. 10 shows that deposition parameters, such as for example the penetration depth below the surface 2.2 of the target substrate 2, the displacement in the target substrate 2 (e.g. displacement of cells in a target tissue) and the orientation of the embedded biological material, can be influenced by the shape and size of the particles. The particles thaw immediately after penetration into the target substrate 2, during movement in the latter or after reaching the deposition position. Penetration depths in the range from a few pm to a few mm or even cm can thus be achieved, with injuries or displacements in the volume of the target substrate 2 being minimized.

A significant advantage of the method according to the invention lies in the fact that the embedding of biological material is not limited to cells or cell groups, but rather it is also possible for frozen solutions, particularly frozen active substances, or materials which are soft or elastic at room temperature, such as for example gels, matrix materials or polymers, to be brought into a rigid shape by freezing and accordingly protected and embedded in a stable manner into the target substrate.

FIG. 11 illustrates in a schematic sectional view different phases of the deposition according to the invention of biological material 1 in a target substrate 2 and subsequent development steps which can be obtained after embedding the biological material 1 in the target substrate 2. In step A, the biological material 1 in the frozen state is moved on a free movement path from the directing device 40 of the deposition apparatus 100 (perspective sub-diagram) to the surface 2.2 of the target substrate 2. Through the application of a driving force, the biological material 1 has upon striking the surface 2.2 a predetermined kinetic energy $W_{kin}$ which enables penetration into the target substrate 2 (e.g. a biological tissue). In step B, the frozen biological material 1 penetrates into the target substrate 2. During penetration, the biological material 1 displaces or destroys minimal parts of the target substrate 2. Advantageously, however, any displacement gaps such as, for example, an entry channel or injuries formed by the particle can be closed and healed quickly due to the small particle size. At the same time, due to the direct contact between the biological material 1 and the target substrate 2, a heat exchange takes place until the biological material 1 has thawed (step C). Any additional substance (culture medium, active substance or growth factor) contained in the biological material 1 diffuses in the process into the area surrounding the deposition site.

Steps D and E illustrate development steps which may optionally occur during the embedding of, for example, stem cells or precursor cells in a biological tissue. Individual differentiated cells can occur in distributed form in the tissue by dissolution and migration of the originally embedded cell group and/or by differentiation of the cells that are present (step D). At the same time or subsequently, physiological tissue types are able to form starting from the individual cells. The start of angiogenesis is illustrated for example in step E.

The clear flight path shown in step A of FIG. 11 for the biological material 1 need not necessarily be provided between the directing device 40 and the surface 2.2 of the target substrate 2, but rather in a modified embodiment of the invention may be formed in a cavity 2.3 of the target substrate 2 (FIG. 12). In this case, the directing device of the deposition apparatus (not shown) comprises an elongate nozzle channel which forms a hollow line, such as for example a cannula, syringe tip or capillary. The directing device can be introduced into the target substrate 2 as far as into the cavity 2.3, such as for example a hollow organ, in order to shoot the biological material 1 from there into the surrounding target substrate 2.

FIG. 12 also illustrates a further variant of the method according to the invention, in which particles comprising different biological materials are successively embedded at a common deposition site in the target tissue 2. Advantageously, certain physiological compositions, e.g. of cells, cell components, biological macromolecules, active substances and/or biocompatible additional substances, e.g. fillers, can thus be provided upon thawing at the deposition site. By way of example, the lowermost particle shown in FIG. 12 comprises a group of stem cells to which there is added, with the middle particle, a culture medium which contains for example differentiation factors. Advantageously, the culture medium can be supplied without cryoprotectant. This allows a rapid dilution of the cryoprotectant contained in the lowermost particle and thus an increased vitality rate of the embedded cells. Finally, a further cell type with a culture solution can be introduced with the uppermost particle, which is intended to influence the differentiation of the stem cells.

FIG. 13 illustrates a further application of the invention in the deposition of biological material 1 in a target substrate 2 which is formed by a cell culture, e.g. in a culture vessel. By means of the deposition apparatus 100, which is shown as a tool suitable for manual handling, the biological material 1 is embedded in the target substrate 2 as a function of the configuration of the nozzle arrangement 41 of the directing device 40 and the movement of the deposition apparatus 100 over the target substrate 2. By way of example, there is shown in A an individual nozzle which is designed for the serial shooting of the biological material 1 into the target substrate 2. In B, there is also shown a nozzle arrangement 41 with a matrix form of the outlet nozzles, which is design for simultaneous shooting or for rapid pattern formation (formation generation) in the target substrate 2. The simultaneous (parallel) embedding of biological material 1 in the target substrate 2 is also advantageous for embedding stem cells in damaged tissue, as used in regenerative medicine.

FIG. 14 illustrates the embedding of biological material in an inhomogeneous target substrate 2 comprising a tissue layer 2.4 and a blood vessel 2.5. Using the nozzle arrangement 41 of the deposition apparatus 100 (sub-diagram), a plurality of samples of the biological material can be embedded in the target substrate 2. When embedding cells which have the property of actively migrating in the biological tissue, such as for example stem cells, fibroblasts or macrophages, these cells can pass over into the blood vessel 2.5 of the treated organism. The position and size of the embedded samples of the biological material 1 can be selected as a function of operating parameters of the deposition apparatus 100 and in particular the configuration of the nozzle arrangement 41.

Figure 15:
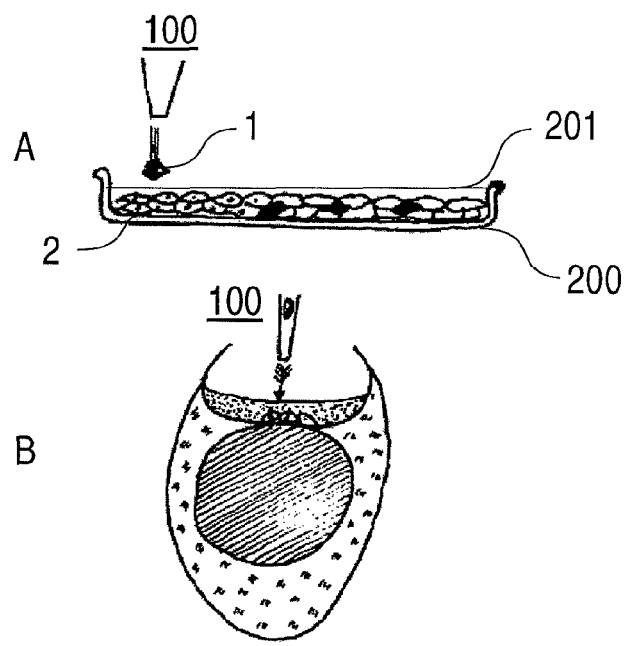

Further examples of the embedding of biological material 1 in cell cultures are shown in FIGS. 15A and 15B. As shown in FIG. 15A, the target substrate 2 comprises a cell culture in a culture vessel 200. The cell culture comprises for example animal or plant cells, bacteria, fungi or mixtures thereof. The cell culture may advantageously be coated with a liquid 201, without impairing the deposition of the biological material 1 according to the invention. In the case of embedding in natural culture devices (FIG. 15B), this is also advantageous if the target substrate 2 is formed by an inhomogeneous system with a phase boundary. The embedding of frozen particles in a bird egg or fish egg is shown schematically by way of example in FIG. 15B. This technique is used in the common culturing of embryonic cells or other cells or tissue parts. In this application, the advantage of the invention lies in the high deposition accuracy and the mechanical protection of the cells until the point of thawing. In a manner differing from the illustrated variant, the deposition of the biological material may also take place in other parts of the natural culture device, e.g. in the egg yolk.

Further application examples of the invention moreover include the introduction of deep-frozen hair root cells or aggregates into the skin of patients, and also the introduction of pigment cells or stem cells in vitro and in vivo.

The features of the invention which are disclosed in the above description, the drawings and the claims may be important both individually and in combination for implementing the invention in its various embodiments.

The invention claimed is:

1. A deposition apparatus which is adapted for depositing biological material in a frozen state in a target substrate, comprising a charging device, a cooling device and a driving device, wherein:
   (a) the charging device is adapted for providing at least one particle of the biological material at the driving device;
   (b) the cooling device is adapted for cooling the biological material, at least a part of the charging device and at least a part of the driving device to a temperature below −130° C.;
   (c) the driving device is a fluid drive adapted for applying a driving force to the at least one particle of the biological material by way of a cooling gas adapted to freeze the biological material;
   (d) the biological material comprises at least one eukaryotic cell;
   (e) the target substrate comprises an isolated biological tissue, a composite composed of at least one of biological tissue and non-biological matrix material, a cell culture, a cell monolayer, a cell multilayer, a matrix material without biological cells, a synthetic cell culture device, a natural cell culture device or living biological tissue in a body of a biological organism;
   (f) the driving device for applying the driving force is formed in such a way that the at least one particle of the biological material can penetrate into the target substrate under an effect of the driving force without causing irreparable injury to the target substrate; and
   (g) there is a clear path from the charging device to the target substrate along which the at least one particle of the biological material is driven.

2. The deposition apparatus according to claim 1, further comprising a preparation device which is adapted for supplying the biological material to the charging device.

3. The deposition apparatus according to claim 2, in which the preparation device contains a droplet generator, which is adapted for generating droplets of the biological material, or a particle generator, which is adapted for generating frozen droplets of the biological material.

4. The deposition apparatus according to claim 1, further comprising a directing device which is adapted for orienting a movement of the biological material towards the target substrate.

5. The deposition apparatus according to claim 4, in which the directing device comprises a nozzle device.

6. The deposition apparatus according to claim 4, in which the directing device comprises a tool suitable for manual handling and having at least one hollow line.

7. The deposition apparatus according to claim 1, wherein: (a) the charging device comprises a sample injector, which is adapted for introducing the biological material into an acceleration line of the driving device; (b) the sample injector comprises an injector cartridge and a droplet dispenser; (c) the sample injector is arranged in the acceleration line and has a longitudinal direction with an inflow opening and an outflow opening, which are designed to be flowed through by a fluid provided by the driving device; and (d) the droplet dispenser is adapted for supplying droplets of the biological material into the acceleration line.

8. The deposition apparatus according to claim 1, wherein: (a) the charging device comprises a sample injector, which is adapted for introducing the biological material into an acceleration line of the driving device; (b) the sample injector comprises an injector cartridge and a particle dispenser; (c) the sample injector is arranged in the acceleration line and has a longitudinal direction with an inflow opening and an outflow opening, which are designed to be flowed through by a fluid provided by the driving device; and (d) the particle dispenser is adapted for supplying particles of the frozen biological material into the acceleration line.

9. The deposition apparatus according to claim 1, wherein: (a) the charging device comprises a sample injector, which is adapted for introducing the biological material into an acceleration line of the driving device; (b) the sample injector comprises an injector cartridge; and (c) the injector cartridge is arranged replaceably in the acceleration line.

10. The deposition apparatus according to claim 1, wherein: (a) the charging device comprises a sample injector, which is adapted for introducing the biological material into an acceleration line of the driving device; (b) the sample injector comprises an injector cartridge; and (c) the injector cartridge is closed by cover elements which can be opened when the driving force of the driving device is applied.

11. The deposition apparatus according to claim 4, wherein the cooling device is adapted for cooling at least part of the directing device.

12. The deposition apparatus according to claim 1, further comprising a control circuit which is connected to the control of at least one of the charging device, the driving device, a preparation device which is adapted for supplying the biological material to the charging device and the cooling device.

13. The deposition apparatus according to claim 12, in which at least one of the charging device, the driving device, the preparation device and the cooling device is adapted for a switched-mode operation.

14. The deposition apparatus according to claim 1, further comprising at least one of:
   an imaging device comprising at least one of a camera device, a microscopy device, an ultrasound device, a stroboscopy device and an endoscopy device, a navigation device which is adapted for positioning the deposition apparatus relative to the target substrate, and a conditioning device comprising at least one of an illumination device and a temperature control device.

15. An injector cartridge which is adapted for providing frozen biological material in a deposition apparatus according to claim 1.

16. The injector cartridge according to claim 15, which is closed by cover elements which can be opened when the driving force of the driving device is applied.

17. A method for depositing biological material in a target substrate, comprising the steps:

providing the biological material in a deposition apparatus of claim 1, applying a driving force to the biological material, and embedding the biological material in a frozen state in the target substrate, the biological material being introduced into the target substrate under the effect of the driving force, wherein: (a) the biological material comprises at least one eukaryotic cell; (b) the target substrate is a biological tissue; (c) the biological material follows a clear path from a charging device to the target substrate; and (d) the cooling device cools the biological material, at least a part of the charging device and at least a part of the driving device to a temperature below −130° C.

18. The method according to claim 17, in which the biological material further comprises at least one biocompatible additional substance.

19. The method according to claim 18, in which the at least one eukaryotic cell and the at least one biocompatible additional substance form at least one of the following compositions:

a composition containing one individual eukaryotic cell which is surrounded by the additional substance, a composition containing a cell group which is surrounded by the additional substance, a composition containing an additional substance which forms a hollow body, in which the at least one eukaryotic cell is arranged, a composition containing an additional substance which is surrounded by eukartyotic cells, and a composition containing the at least one eukaryotic cell, the at least one additional substance and a solid carrier material.

20. The method according to claim 17, in which the biological material comprises at least one member selected from the group consisting of stem cells, precursor cells, differentiated cells, tumor-influencing cells, nerve cells, muscle cells, cartilage cells, bone cells, islet cells, gland cells, endothelial cells and epithelial cells.

21. The method according to claim 17, in which the target substrate is arranged outside a body of a biological organism.

22. The method according to claim 17, in which the driving force is applied to the biological material by at least one of a flowing fluid and a mechanical driving element.

23. The method according to claim 22, in which a predetermined driving force is applied to the biological material in such a way that the biological material is positioned in the target substrate at a predetermined penetration depth.

24. The method according to claim 23, in which the driving force is set by a control circuit.

25. The method according to claim 17, in which different cell types are positioned in the target substrate one after the other.

26. The method according to claim 17, in which the biological material is positioned in the target substrate with a predetermined geometric pattern.

27. The method according to claim 26, in which the geometric pattern is set by means of a nozzle device, from which the biological material moves towards the target substrate.

28. The method according to claim 17, in which the biological material is transformed into the frozen state before the driving force is applied.

29. The method according to claim 28, further comprising the step of freezing droplets of a cell suspension.

30. The method according to claim 29, in which hanging droplets of the cell suspension are frozen.

31. The method according to claim 28, in which droplets of the cell suspension are frozen on a hydrophobic underlayer.

32. The method according to claim 17, in which the biological material is transformed into the frozen state during or after the application of the driving force.

33. The method according to claim 17, further comprising at least one of the further steps:

monitoring the target substrate by means of an imaging process using at least one of a camera device, ultrasound, NMR and microscopy, heating the target substrate after the biological material has been deposited, and reducing a temperature of the target substrate prior to the embedding of the biological material.

34. Method of modifying biological tissue, said method comprising:

providing a biological material, which contains at least one eukaryotic cell, in the frozen state in a deposition apparatus of claim 1;

applying a driving force to the biological material; and embedding the biological material in a frozen state in the biological tissue to modify the biological tissue, wherein the biological material is driven by the driving force along a clear path to the biological tissue.

* * * * *